(12) United States Patent
Brand et al.

(10) Patent No.: US 7,191,777 B2
(45) Date of Patent: Mar. 20, 2007

(54) MEDICAMENT DISPENSER

(75) Inventors: Peter John Brand, Ware (GB); James William Godfrey, Ware (GB); Paul Kenneth Rand, Ware (GB)

(73) Assignee: Glaxo Group Limited, Greenford (GB)

( * ) Notice: Subject to any disclaimer, the term of this patent is extended or adjusted under 35 U.S.C. 154(b) by 270 days.

(21) Appl. No.: 10/311,562

(22) PCT Filed: Jul. 11, 2001

(86) PCT No.: PCT/EP01/07968

§ 371 (c)(1),
(2), (4) Date: Dec. 16, 2002

(87) PCT Pub. No.: WO02/05879

PCT Pub. Date: Jan. 24, 2002

(65) Prior Publication Data

US 2003/0183226 A1    Oct. 2, 2003

(30) Foreign Application Priority Data

Jul. 15, 2000 (GB) .............................. 0017301.3
Aug. 22, 2000 (GB) .............................. 0020538.5

(51) Int. Cl.
     *A61M 11/00*      (2006.01)
     *A61M 15/00*      (2006.01)
     *A62B 9/00*      (2006.01)

(52) U.S. Cl. .......................... 128/200.23; 128/203.15; 128/205.23

(58) Field of Classification Search .......... 128/200.14, 128/200.23, 200.22, 203.12, 202.22, 204.21, 128/204.23, 205.23
See application file for complete search history.

(56) References Cited

U.S. PATENT DOCUMENTS

| | | | |
|---|---|---|---|
| 4,679,426 A | 7/1987 | Fuller et al. | |
| 4,724,427 A | 2/1988 | Carroll et al. | |
| 4,817,822 A * | 4/1989 | Rand et al. | 222/38 |
| 4,940,966 A | 7/1990 | Pettigrew et al. | 340/551 |
| 5,025,246 A | 6/1991 | Schenkel et al. | |
| 5,321,619 A | 6/1994 | Matsuda et al. | |
| 5,347,274 A | 9/1994 | Hassett | |
| 5,363,842 A * | 11/1994 | Mishelevich et al. | 128/200.14 |
| 5,368,948 A | 11/1994 | Davies et al. | |
| 5,381,137 A | 1/1995 | Ghaem et al. | |
| 5,381,859 A | 1/1995 | Minakami et al. | |
| 5,448,110 A | 9/1995 | Tuttle et al. | |
| 5,469,363 A | 11/1995 | Saliga et al. | |
| 5,491,473 A | 2/1996 | Gilbert | |

(Continued)

FOREIGN PATENT DOCUMENTS

DE      19621179      11/1997

(Continued)

*Primary Examiner*—Henry Bennett
*Assistant Examiner*—Amadeus Lopez
(74) *Attorney, Agent, or Firm*—James P. Riek (57) ABSTRACT

A medicament dispenser for use in the storage, presentation and/or dispensing of medicament comprising a body shaped for receipt of a medicament container. In association with the body, there is a first transceiver for transmitting and receiving data. A medicament container is receivable by the body. In association with the medicament container, there is a second transceiver for transmitting and receiving data. Data is transferable in two-way fashion from the first transceiver to the second transceiver. The medicament dispenser may be supplied in kit of parts form.

10 Claims, 6 Drawing Sheets

U.S. PATENT DOCUMENTS

| | | | |
|---|---|---|---|
| 5,505,195 A | 4/1996 | Sallis et al. | |
| 5,507,277 A * | 4/1996 | Rubsamen et al. | 128/200.14 |
| 5,508,203 A | 4/1996 | Fuller et al. | |
| 5,516,692 A | 5/1996 | Berndt et al. | |
| 5,520,166 A * | 5/1996 | Ritson et al. | 128/200.14 |
| 5,528,221 A | 6/1996 | Jeuch et al. | |
| 5,541,604 A | 7/1996 | Meier et al. | |
| 5,542,410 A * | 8/1996 | Goodman et al. | 128/200.14 |
| 5,549,101 A * | 8/1996 | Trofast et al. | 128/203.15 |
| 5,560,353 A | 10/1996 | Willemot et al. | |
| 5,582,795 A | 12/1996 | Nishina et al. | |
| 5,583,819 A | 12/1996 | Roesner et al. | |
| 5,587,578 A | 12/1996 | Serra | |
| 5,608,739 A | 3/1997 | Snodgrass et al. | |
| 5,629,981 A | 5/1997 | Nerlikar | |
| 5,682,143 A | 10/1997 | Brady et al. | |
| 5,706,801 A | 1/1998 | Remes et al. | |
| 5,755,218 A * | 5/1998 | Johansson et al. | 128/200.14 |
| 5,770,455 A | 6/1998 | Cargill et al. | |
| 5,771,657 A | 6/1998 | Rice et al. | |
| 5,774,875 A | 6/1998 | Medeiros et al. | |
| 5,777,303 A | 7/1998 | Berney | |
| 5,792,668 A | 8/1998 | Fuller et al. | |
| 5,796,602 A | 8/1998 | Wellan et al. | |
| 5,799,651 A * | 9/1998 | Garby et al. | 128/200.23 |
| 5,809,997 A * | 9/1998 | Wolf | 128/200.23 |
| 5,813,397 A * | 9/1998 | Goodman et al. | 128/200.14 |
| 5,821,524 A | 10/1998 | Horlbeck et al. | |
| 5,844,802 A | 12/1998 | Lepper et al. | |
| 5,874,214 A | 2/1999 | Nova et al. | |
| 5,874,896 A | 2/1999 | Lowe et al. | |
| 5,892,441 A | 4/1999 | Woolley et al. | |
| 5,898,370 A | 4/1999 | Reymond | |
| 5,920,054 A | 7/1999 | Uber | |
| 5,955,950 A | 9/1999 | Gallagher et al. | |
| 5,959,531 A | 9/1999 | Gallagher et al. | |
| 5,961,925 A | 10/1999 | Ruediger et al. | |
| 5,963,136 A | 10/1999 | O'Brien et al. | |
| 5,972,156 A | 10/1999 | Brady et al. | |
| 5,981,166 A | 11/1999 | Mandecki et al. | |
| 5,986,562 A | 11/1999 | Nikolich et al. | |
| 6,002,344 A | 12/1999 | Bandy et al. | |
| 6,008,727 A | 12/1999 | Want et al. | |
| 6,017,496 A | 1/2000 | Nova et al. | |
| 6,018,299 A | 1/2000 | Eberhardt et al. | |
| 6,025,780 A | 2/2000 | Bowers et al. | |
| 6,032,666 A | 3/2000 | Davies et al. | |
| 6,040,773 A | 3/2000 | Vega et al. | |
| 6,040,774 A | 3/2000 | Schepps et al. | |
| 6,046,003 A | 4/2000 | Mandecki et al. | |
| 6,049,278 A | 4/2000 | Guthrie et al. | |
| 6,078,845 A | 6/2000 | Friedman et al. | |
| 6,147,604 A | 11/2000 | Hugh et al. | |
| 6,148,815 A * | 11/2000 | Wolf | 128/205.23 |
| 6,202,642 B1 * | 3/2001 | McKinnon et al. | 128/200.23 |
| 6,259,654 B1 | 7/2001 | de la Huerga | |
| 6,294,999 B1 | 9/2001 | Yarin et al. | |
| 6,366,824 B1 | 4/2002 | Nair et al. | |
| 6,594,611 B2 | 7/2003 | Beffa | |
| 6,729,327 B2 * | 5/2004 | McFarland, Jr. | 128/203.12 |
| 6,729,330 B2 * | 5/2004 | Scarrott et al. | 128/205.23 |
| 6,839,604 B2 | 1/2005 | Godfrey | |
| 6,958,691 B1 * | 10/2005 | Anderson et al. | 340/539.12 |
| 7,091,864 B2 * | 8/2006 | Veitch et al. | 340/572.8 |
| 7,111,756 B2 * | 9/2006 | Grey et al. | 222/21 |
| 2002/0198618 A1 | 12/2002 | Madden et al. | |
| 2003/0011476 A1 | 1/2003 | Godfrey et al. | |
| 2003/0064029 A1 | 4/2003 | Tarara et al. | |
| 2003/0079744 A1 * | 5/2003 | Bonney et al. | 128/203.12 |
| 2003/0183697 A1 | 10/2003 | Porter | |
| 2004/0025871 A1 * | 2/2004 | Davies | 128/203.12 |
| 2004/0100415 A1 | 5/2004 | Veitch et al. | |

FOREIGN PATENT DOCUMENTS

| | | |
|---|---|---|
| DE | 19753619 | 5/1999 |
| DE | 19806049 | 8/1999 |
| DE | 19826568 | 12/1999 |
| DE | 29915334 | 1/2000 |
| EP | 645631 | 3/1995 |
| EP | 727752 | 8/1996 |
| EP | 786357 | 7/1997 |
| EP | 831410 | 3/1998 |
| EP | 853288 | 7/1998 |
| EP | 859299 | 8/1998 |
| EP | 895087 | 2/1999 |
| EP | 908840 | 4/1999 |
| EP | 947952 | 10/1999 |
| EP | WO 00/03313 | 1/2000 |
| FR | 2656446 | 6/1991 |
| FR | 2760209 | 9/1998 |
| GB | 2076259 | 9/1981 |
| GB | 2249001 | 4/1992 |
| GB | 2262452 | 6/1993 |
| GB | 2297225 | 7/1996 |
| GB | 2308947 | 7/1997 |
| GB | 2312595 | 10/1997 |
| GB | 2314418 | 12/1997 |
| GB | 2328281 | 2/1999 |
| JP | 08195697 | 7/1996 |
| JP | 10013295 | 1/1998 |
| JP | 10040329 | 2/1998 |
| JP | 10049620 | 2/1998 |
| JP | 10123147 | 5/1998 |
| JP | 11304812 | 11/1999 |
| JP | 11352243 | 12/1999 |
| WO | WO 92/12402 | 7/1992 |
| WO | WO 92/17231 | 10/1992 |
| WO | WO 94/07225 | 3/1994 |
| WO | WO 95/22365 | 8/1995 |
| WO | WO 96/31790 | 10/1996 |
| WO | WO 97/04338 | 2/1997 |
| WO | WO 97/07443 | 2/1997 |
| WO | WO 97/10896 | 3/1997 |
| WO | WO 98/05088 | 2/1998 |
| WO | WO 98/15853 | 4/1998 |
| WO | WO 98/26312 | 6/1998 |
| WO | WO 98/35243 | 8/1998 |
| WO | WO 98/46548 | 10/1998 |
| WO | WO 99/35091 | 7/1999 |
| WO | WO 99/35516 | 7/1999 |
| WO | WO 99/48044 | 9/1999 |
| WO | WO 99/49408 | 9/1999 |
| WO | WO 99/50690 | 10/1999 |
| WO | 9965548 | 12/1999 |
| WO | WO 99/65002 | 12/1999 |
| WO | WO 99/67099 | 12/1999 |
| WO | WO 00/21030 | 4/2000 |
| WO | WO 00/21031 | 4/2000 |
| WO | WO 00/21032 | 4/2000 |
| WO | 0025720 | 5/2000 |
| WO | WO 01/24690 | 4/2001 |
| WO | WO 01/63368 | 8/2001 |

* cited by examiner

MEDICAMENT DISPENSER

CROSS-REFERENCE TO RELATED APPLICATIONS

This application is filed pursuant to 35 USC 371 as a United States National Phase Application of International Patent Application Serial No. PCT/EP01/07968 filed 11 Jul. 2001, which claims priority from GB0017301.3 filed on 15 Jul. 2000 in the United Kingdom, and GB0020538.5 filed on 22 Aug. 2000 in the United Kingdom.

FIELD OF THE INVENTION

The present invention relates to a medicament dispenser for use in the dispensing of medicament. The medicament dispenser has a medicament container (e.g. in the form of a reloadable cartridge).

BACKGROUND OF THE INVENTION

Medical dispensers are well known for the dispensing of various kinds of medicament. Inhalation devices, such as metered dose inhalers (MDI) and dry powder inhalers are known for the delivery of medicament for the treatment of respiratory disorders. Syringes, including needleless syringes are also known for the delivery of injectable medicament to a patient.

The manufacture of medical dispensers requires careful control to ensure compliance with product specifications. Similarly, the packaging, distribution and sale of medical dispensers are carefully controlled to ensure consistent product quality and security for the patient. It is common practice to mark the dispenser and any packaging therefor with various codings and serial numbers for use in checking product integrity. Widely used marking techniques include the use of visual text, machine-readable text, bar codes and dot codes.

In the event of a patient complaint which results in return of the medical dispenser or indeed in the event of a product recall for any other reason, the manufacturer employs the codings and serial numbers to check the product details. Counterfeiting is known to be a problem with medical dispensers given the often-high resale value of the product. Product marking is further employed to reduce the opportunities for counterfeiting and in particular, to make counterfeit products more readily identifiable.

Reloadable medicament dispensers are known. These typically comprise a housing defining a cavity and a medicament container which is reversibly receivable thereby. The housing and the medicament container may be sold separately or as a kit of parts. There is current interest in the development of reloadable medicament dispensers in which the housing is reasonably sophisticated in nature and comprises some sort of electronic data management capability. The reload is desirably in the form of a medicament cartridge which for cost reasons has a relatively simple form. The patient retains the sophisticated actuator housing and reloads are inserted as required.

There are a number of potential challenges associated with reloadable medicament dispensers and these have hitherto prevented their widespread use. A primary challenge is to ensure that the reload is employed with the correct actuator housing. Secondary challenges include preventing the use of out-of-date or counterfeit cartridge reloads. Tailoring the actuator housing to be only operable (e.g. mechanically operable) with the correct reload is a feasible, but expensive and therefore commercially unattractive solution to the primary challenge. Existing product marking methods can in some ways be employed to address the secondary challenges. Overall, there is a need for further developments to address these and other challenges associated with reloadable medicament dispensers.

The Applicants have now devised a solution for addressing the potential challenges associated with reloadable medicament dispensers which is of greater sophistication than presently used techniques and has significant advantages thereover. The solution involves associating a first transceiver for transmitting and receiving a data signal with the reloadable actuator housing and associating a second transceiver with the medicament container reload. The first and second transceivers are arranged such that data is transferable in two-way fashion (e.g. read/write fashion) therebetween. In typical embodiments, the first transceiver is an actively powered transceiver which forms an integral part of an electronic data management system on the housing and the second transceiver is a passive (i.e. not directly powered) transceiver. Thus, the second transceiver may for example be a magnetic or radiofrequency identifier (RFID) label and the first transceiver a reader therefor having read/write capability.

The transceiver on the medicament reload is typically marked at the time of manufacture with various product information including type of medicament, initial number of doses, date and place of manufacture and an anti-counterfeiting code. If desired, further marking can be added at the time of dispensing such as date and time of dispensing, name of the prescriber and pharmacist and identification of the patient. When the reload is inserted into the actuator housing, the marking thereon will be read by the transceiver on the housing and the electronic data management system updated. At this point, various security, product integrity and product matching with actuator checks may be conducted (e.g. for out-of-date reloads or counterfeits) and any problems flagged. If product integrity problems are detected the dispenser may automatically shutdown.

An important aspect of the present development is that it allows for two-way transfer of data between the transceiver and electronic data management system on the housing and the transceiver on the medicament reload. This gives rise to significant advantages. For example, each time the medicament dispenser is used by the patient actuation or dispensing data may be recorded and transferred to the reload. The dose count and other compliance data are therefore recordable by both the electronic data management system of the housing and on the reload. When the reload is removed from the housing, any subsequent insertion thereof can be arranged to result in a re-recognition of the reload and associated update of the electronic data management system. This can be arranged to operate even when multiple, possibly dissimilar, reloads are used with the same actuator housing. The development described herein therefore enables a sophisticated actuator with electronic data management capability to be used securely and intelligently with multiple medicament reloads over a period of time.

PCT patent application no. WO92/17231 describes a metered dose inhaler having a microelectronic assembly thereon. The medicament container includes a set of electrically conducting strips which represent information about the medicament container in digital form. The housing of the device includes electrical contact fingers which are contactable with the strips to enable reading of the information to a microelectronic memory on the housing. Read/write communication would not be possible between the fingers and the reader and the significant advantages of the present invention would therefore not be achievable with this inhaler. Furthermore, contact between the strips on the container and the electrical contact fingers is required which requires physical tailoring of the container to the housing, thereby limiting product design options.

This document also describes an embodiment in which an active (i.e. powered) microelectronic element is attached to the container.

SUMMARY OF THE INVENTION

According to one aspect of the present invention there is provided a medicament dispenser comprising a body, said body shaped for receipt of a medicament container; in association with the body, a first transceiver for transmitting and receiving data; a medicament container receivable by the body; and in association with the medicament container, a second transceiver for transmitting and receiving data, wherein data is transferable in two-way fashion from the first transceiver to the second transceiver.

The medicament dispenser herein is suitable for use in the storage and/or presentation and/or dispensing of medicament.

The body is typically shaped to define a cavity within which the medicament container is receivable. The body and/or medicament container may be further shaped with any manner of grooves, indentations or other shaping or surface details to define a 'lock and key' relationship between the body and the container. Colour guides, arrows and any other surface markings may also be employed.

The data is preferably in digital form and suitable for transfer by e.g. electronic or optical means. Data is transferable when the medicament container is received wholly or partly by the body. A defined data transfer position in which there is specific registration between the body and container received thereby may be established.

One advantage of the present invention is the ability to store many types of information in different parts of the memory structure of the transceivers. The information is furthermore stored in a form which is readily and accurately transferable.

The information could for example, include manufacturing and distribution compliance information written to the memory at various points in the manufacturing or distribution process, thereby providing a detailed and readily accessible product history of the dispenser. Such product history information may, for example, be referred to in the event of a product recall. The compliance information could, for example, include date and time stamps. The information could also include a unique serial number stored in encrypted form or in a password protectable part of the memory which uniquely identifies the product and therefore may assist in the detection and prevention of counterfeiting. The information could also include basic product information such as the nature of the medicament and dosing information, customer information such as the name of the intended customer, and distribution information such as the intended product destination.

The information written to the memory may be provided in a particular language (e.g. French, English) including a non-latin typescript language (e.g. Mandarin Chinese or Thai) or it may be provided in multilingual form. In one aspect, the dispenser is provided with the capability (e.g. by way of appropriate software) to display information read from the medicament container in any selected language.

In one aspect, the information/language is defined by what is written to the medicament container (e.g. at the traditional point of labelling in the manufacturing process). The container then has the form of a geography and/or language-specific product.

In another aspect, the medicament container has multi-geographic and/or linguistic information written thereto (e.g. at the traditional point of labelling point in the manufacturing process). The container then has the form of an 'international' product. The medicament dispenser may then be configured (e.g. by the patient or by the pharmacist at the time of prescribing) to read/display to the patient only that information/language data set that is relevant to the particular market (or patient) of interest.

In a further aspect, the medicament container has information written thereto (e.g. at the traditional point of labelling in the manufacturing process) in a default (e.g. standard) language/character set. The container then has the form of a 'standard' product. The medicament dispenser is then provided with the capability translate that standard dataset into any local format such that it displays to the patient only the information/language data set that is relevant to the particular market (or patient) of interest.

On loading or reloading the dispenser with a medicament container (such as an aerosol canister or dry powder cassette) the second transceiver may, for example, read the unique serial number, batch code and expiry date of the medicament and any other information on the second transceiver. In this way the nature and concentration of the medicament, together with the number of doses used or remaining within the container, may be determined. This information can be displayed to the patient on a visual display unit. Other information, such as the number of times the dispenser has been reloaded with a medicament container, may also be displayed.

Similarly, should the container be removed from the housing before the supply of medicament is exhausted, the same data can be read from the second transceiver and the number of doses remaining or used determined. Other information, such as the date and time of administration of the drug, or environmental exposure data such as the minimum/maximum temperatures or levels of humidity the medicament container has been exposed to, may also be read and displayed to the user.

In the event that the supply of medicament within the container becomes exhausted, or that the shelf life of the medicament has expired, or that the first transceiver does not recognise the batch code on the second transceiver, activation of the dispenser may be prevented to safeguard the user. Activation may also be prevented if the medicament has been exposed to extreme environmental conditions for periods outwith the manufacturer's guidelines.

Data may be transferred to and from any transceiver during the period of use of the medicament dispenser by the patient. For example, the medicament dispenser may include an electronic data management system having various sensors associated therewith. Any data collected by the sensors or from any data collection system associated with the electronic data management system including a clock or other date/time recorder is transferable.

Data may be transferred each time the patient uses the device. Or alternatively, data may be stored in a database memory of the electronic data management system and periodically downloaded to any transceiver. In either case, a history of the usage of the device may be built up in the memory of a transceiver.

In one embodiment herein, a history of the usage of the medicament dispenser is transferred to the second transceiver on the aerosol container. When the medicament container is exhausted it is exchanged by the patient for a new refill container. At the point of exchange, which will typically occur at the pharmacy, data may be transferred from the exhausted container to the refill and vice-versa. Additionally, usage history data may be read from the refill and transferred to a healthcare data management system for example comprising a network computer system under the control of a healthcare data manager.

Methods are envisaged herein whereby the patient is given some sort of reward for returning the refill and making available the data comprised within the second transceiver. Methods are also envisaged herein whereby the healthcare data manager is charged for either receipt of the data from the second transceiver or for its use for commercial purposes. Any rewards or charging may be arranged electronically. The methods may be enabled by distributed or web-based computer network systems in which any collected data is accessible through a hub on the network. The hub may incorporate various security features to ensure patient confidentiality and to allow selective access to information collected dependent upon level of authorisation. The level of user authorisation may be allocated primarily to safeguard patient confidentiality. Beyond this the level of user authorisation may also be allocated on commercial terms with for example broader access to the database being authorised in return for larger commercial payments.

Suitably, the first and second transceiver each comprise an antenna or equivalent for transmitting or receiving data and connecting thereto a memory. The antenna can, in embodiments, also transfer energy to the passive receiver.

The memory will typically comprise an integrated circuit chip. Either transceiver may be configured to have a memory structure which allows for large amounts of information to be stored thereon. The memory structure can be arranged such that parts of the memory are read-only, being programmed during/after manufacture, other parts are read/write and further parts are password protectable. Initial transfer of information (e.g. on manufacture or one dispensing) to or from any transceiver can be arranged to be readily achievable by the use of a reader which is remote from the medical dispenser, thereby minimising the need for direct product handling. In further aspects, the reader can be arranged to simultaneously read or write to the memory of multiple transceivers on multiple medicament dispensers.

A suitable power source such as a battery, clockwork energy store, solar cell, fuel cell, kinetics-driven cell or mains power supply (e.g. via a suitable transformer) will be provided as required to any electronic component herein. The power source may be arranged to be rechargeable or reloadable.

Suitably, data is transferable in two-way fashion between the first and second transceiver without the need for direct physical contact therebetween. Preferably, data is transferable wirelessly between the first and second transceiver.

Suitably, the first transceiver is an active transceiver and the second transceiver is a passive transceiver. The term active is used to mean directly-powered and the term passive is used to mean indirectly-powered.

Suitably, the second transceiver comprises a label or tag comprising an antenna for transmitting or receiving energy; and an integrated circuit chip connecting with said antenna, and the first transceiver comprises a reader for said label or tag. In this case the label or tag is a passive transceiver and the reader is an active transceiver. Preferably, the reader will not need to be in direct contact with the tag or label to enable the tag or label to be read.

The tag may be used in combination and/or integrated with other traditional product labelling methods including visual text, machine-readable text, bar codes and dot codes.

Suitably, the integrated circuit chip has a read only memory area.

Suitably, the integrated circuit chip has a memory area with restricted read access.

Suitably, the integrated circuit chip has a read/write memory area.

Suitably, the integrated circuit chip has a one-time programmable memory area. More preferably, the one-time programmable memory area contains a unique serial number.

Suitably, the integrated circuit chip has a preset memory area containing a factory preset, non-changeable, unique data item. The preset memory item is most preferably in encrypted form.

Suitably, the integrated circuit chip has plural memory areas thereon.

Suitably, any memory area contains data in encrypted form. Electronic methods of checking identity, error detection and data transfer may also be employed.

Suitably, any memory area is password protected.

In one preferred aspect, the integrated circuit has plural memory areas thereon including a read only memory area containing a unique serial number, which may for example be embedded at the time of manufacture; a read/write memory area which can be made read only once information has been written thereto; and a password protected memory area containing data in encrypted form which data may be of anti-counterfeiting utility.

The tag may be associated with the medicament container in any suitable fashion. In one aspect, the tag is somehow attached or fixed to the medicament container by any suitable means including adhesive fixing, welding, snap-fit arrangements or through the use of various mounting means. The mounting means may for example, comprise an adhesive label, wrap-round tape or collar arrangement.

In another aspect, the tag is located within the medicament container, for example, as a loose component together with any medicament contents thereof or within a separate compartment or housing within the medicament container. An advantage of placing the tag within the medicament container is that is can be 'hidden from view' thereby improving its utility as a security feature. Additionally, the tag and container may be configured (e.g. shaped and sized) such that the tag may only be removed by rupture or other degradation of the medicament container or tag.

Suitably, the tag is on a carrier and the carrier is mountable on the housing or the medicament container.

In one aspect, the carrier is a flexible label. In another aspect, the carrier is a rigid disc. In a further aspect, the carrier is a rectangular block. In a further aspect, the carrier is a collar (e.g. in the form of a ring) suitable for receipt by (e.g. for mounting to) the medicament container. Other shapes of carrier including those defining chip housings or enclosures are also envisaged.

Suitably, the carrier is mouldable or weldable to the medicament container or housing.

Suitably, the carrier encases the tag. More preferably, the carrier forms a hermetic seal for the tag.

In one aspect, the carrier comprises an insulating material such as a glass material or, a paper material, a ceramic material or an organic polymeric material such as polypropylene.

Alternatively, the carrier includes a ferrite material.

The energy to power any transceiver may be in any suitable form including ultrasonic, infrared, radiofrequency, magnetic, optical and laser form. Any suitable channels may be used to channel the energy including wave guide and fibre optic channels.

In one aspect, the second transceiver comprises a radiofrequency identifier comprising an antenna for transmitting or receiving radiofrequency energy; and an integrated circuit chip connecting with said antenna, and the first transceiver comprises a reader for said radiofrequency identifier. In this case the radiofrequency identifier is a passive transceiver and the reader is an active transceiver. An advantage of radiofrequency identifier technology is that the reader need not be in direct contact with the radiofrequency identifier tag or label to be read.

The radiofrequency identifier can be any known radiofrequency identifier. Such identifiers are sometimes known as radiofrequency transponders or radiofrequency identification (RFID) tags or labels. Suitable radiofrequency identifiers include those sold by Phillips Semiconductors of the Netherlands under the trade marks Hitag and Icode, those sold by Amtech Systems Corporation of the United States of America under the trade mark Intellitag, and those sold by Texas Instruments of the United States of America under the trade mark Tagit.

Suitably, the antenna of the RFID tag is capable of transmitting or receiving radiofrequency energy having a frequency of from 100 KHz to 2.5 GHz. Preferred operating frequencies are selected from 125 KHz, 13.56 MHz and 2.4 GHz.

In one aspect, the second transceiver comprises a magnetic label or tag comprising an antenna for transmitting or receiving magnetic field energy; and an integrated circuit chip connecting with said antenna, and the first transceiver comprises a reader for said magnetic label or tag. In this case the magnetic label or tag is a passive transceiver and the reader is an active transceiver.

A suitable magnetic label or tag comprises plural magnetic elements in mutual association whereby the magnetic elements move relative to each other in response to an interrogating magnetic field. A magnetic label or tag of this type is described in U.S. Pat. No. 4,940,966. Another suitable magnetic label or tag comprises a magnetorestrictive element which is readable by application of an interrogating alternating magnetic field in the presence of a magnetic bias field which results in resonance of the magnetorestrictive elements at different predetermined frequencies. A magnetic label of this type is described in PCT Patent Application No. WO92/12402. Another suitable magnetic label or tag comprising plural discrete magnetically active regions in a linear array is described in PCT Patent Application No. WO96/31790. Suitable magnetic labels and tags include those making use of Programmable Magnetic Resonance (PMR) (trade name) technology.

In another aspect, the second transceiver comprises a passive microelectronic memory chip and the first transceiver comprises an active reader for said microelectronic memory chip. The microelectronic memory chip may comprise an Electrically Erasable Programmable Read Only Memory (EEPROM) chip or a SIM card-type memory chip. In this case the microelectronic memory chip is a passive transceiver and the reader is an active transceiver.

Any transceiver herein, particularly a passive transceiver may be mounted on or encased within any suitable inert carrier. The carrier may comprise a flexible sheet which may in embodiments be capable of receiving printed text thereon.

In one aspect, the first transceiver is integral with the body such that a single unit is comprised. The first transceiver may for example be encased within or moulded to the body.

In another aspect, the first transceiver forms part of a base unit which is reversibly associable with the body. The base unit may for example, form a module receivable by the body such as a snap-in module.

Suitably, the medicament dispenser additionally comprises an electronic data management system, wherein the electronic data management system is in association with the first transceiver and/or second transceiver. The electronic data management system has input/output capability and comprises a memory for storage of data; a microprocessor for performing operations on said data; and a transmitter for transmitting a signal relating to the data or the outcome of an operation on the data.

Suitably, the electronic data management system is arranged to be responsive to or activated by the voice of a user. Thus, for example the system may be switched on or off in response to a voice command.

In one aspect, the electronic data management system is integral with the body.

In another aspect, the electronic data management system and first transceiver form part of a base unit which is reversibly associable with the body.

Suitably, the medicament dispenser and/or medicament container is provided with release means for releasing medicament from the medicament container.

In some embodiments, the release means needs to be primed to a release position. A prime detector may therefore be provided to detect movement of the release means to the actuation position.

An example of a release means having a priming step is where the medicament dispenser comprises a reservoir of medicament product (e.g. in dry powder form) and the priming step involves movement of a measured dose from the reservoir to the actuation position. Reservoir-based inhalation devices are for example, well known in the art.

Suitably, the medicament dispenser additionally comprises an actuation detector for detecting actuation of the release means wherein said actuation detector transmits actuation data to the electronic data management system.

Suitably, the medicament dispenser additionally comprises a safety mechanism to prevent unintended multiple actuations of the release means. The patient is thereby protected from inadvertently receiving multiple doses of medicament in a situation where they take a number of short rapid breaths. More preferably, the safety mechanism imposes a time delay between successive actuations of the release means. The time delay is typically of the order of from three to thirty seconds.

An example of a release means having a priming step is where the medicament dispenser comprises an energy store which is primed by the user and arranged to release that energy on operation of a trigger. The release of the stored energy results in actuation of the medicament release means. The energy store comprises in preferred aspects, a biasable resilient member such as a spring, a source of compressed fluid such as a canister of compressed gas or a battery. Chemical energy sources are also suitable and might include chemical propellant or ignition mixtures. Other sources might include physical explosives such as liquefied or solidified gas in a canister which burst when heated or exposed to the atmosphere.

Breath-operable inhalers (BoIs) are well-known examples of medicament dispenser having a stored energy system and in which the trigger comprises a breath trigger which is triggered by the breath of the patient. Known BoIs are of the metered dose inhaler (MDI) type where the medicament container comprises an aerosol canister.

Suitably, the medicament dispenser additionally comprises a release detector for detecting release of medicament from the medicament container, wherein said release detector transmits release data to the electronic data management system.

Suitably, any actuation detector, prime detector or release detector comprises a sensor for detecting any suitable parameter such as movement. Any suitable sensors are envisaged including the use of optical sensors. The release detector may sense any parameter affected by release of the medicament such as pressure, temperature, sound, moisture, and chemical factors such as carbon dioxide concentration or oxygen concentration, or the presence of released medicament or propellant (e.g. via an 'electronic nose' sensor).

Suitably, the medicament dispenser additionally comprises a communicator for wireless communication with a network computer system to enable transfer of data between the network computer system and the electronic data management system. Preferably, the communicator enables two-way transfer of data between the network computer system and the electronic data management system.

Suitably, the data is communicable between the network computer system and the electronic data management system in encrypted form. All suitable methods of encryption or partial encryption are envisaged. Password protection may also be employed. Suitably, the communicator employs radiofrequency or optical signals.

In one aspect, the communicator communicates via a gateway to the network computer system. In another aspect, the communicator includes a network server (e.g. a web server) such that it may directly communicate with the network.

In a further aspect, the communicator communicates with the gateway via a second communications device. Preferably, the second communications device is a telecommunications device, more preferably a cellular phone or pager. Preferably, the communicator communicates with the second communications device using spread spectrum radiofrequency signals. A suitable spread spectrum protocol is the Bluetooth (trade mark) standard which employs rapid (e.g. 1600 times a second) hopping between plural frequencies (e.g. 79 different frequencies). The protocol may further employ multiple sending of data bits (e.g. sending in triplicate) to reduce the effects of external interference.

In one aspect, the network computer system comprises a public access network computer system. The Internet is one suitable example of a public access network computer system, wherein the point of access thereto can be any suitable entrypoint including an entrypoint managed by an Internet service provider. The public access network computer system may also form part of a telecommunications system, which may itself be either a traditional copper wire system, a cellular system or an optical network.

In another aspect, the network computer system comprises a private access network computer system. The private access network system may for example, comprise an Intranet or Extranet which may for example, be maintained by a health service provider or medicament manufacturer. The network may for example include password protection; a firewall; and suitable encryption means.

Preferably, the communicator enables communication with a user-specific network address in the network computer system.

The user-specific network address may be selected from the group consisting of a web-site address, an e-mail address and a file transfer protocol address. Preferably, the user-specific network address is accessible to a remote information source such that information from said remote information source could be made available thereto. More preferably, information from the user-specific network address can be made available to the remote information source.

In one aspect, the remote information source is a medicament prescriber, for example a doctor's practice. Information transferred from the medicament prescriber may thus, comprise changes to prescription details, automatic prescription updates or training information. Information transferred to the medicament prescriber may comprise compliance information, that is to say information relating to the patient's compliance with a set prescribing programme. Patient performance information relating for example, to patient-collected diagnostic data may also be transferred to the medicament prescriber. Where the dispenser is an inhaler for dispensing medicament for the relief of respiratory disorders examples of such diagnostic data would include breath cycle data or peak flow data.

In another aspect, the remote information source is a pharmacy. Information transferred from the pharmacy may thus, comprise information relating to the medicament product. Information sent to the pharmacy may thus include prescription requests which have been remotely pre-authorized by the medicament prescriber.

In a further aspect, the remote information source is an emergency assistance provider, for example a hospital accident and emergency service or an emergency helpline or switchboard. The information may thus, comprise a distress or emergency assist signal which requests emergency assistance.

In a further aspect, the remote information source is a manufacturer of medicament or medicament delivery systems. Information transferred to the system may thus, comprise product update information. The system may also be configured to feed information back to the manufacturer relating to system performance.

In a further aspect, the remote information source is a research establishment. In a clinical trial situation, information may thus be transferred relating to the trial protocol and information relating to patient compliance fed back to the research establishment.

In a further aspect, the remote information source is an environmental monitoring station. Information relating to weather, pollen counts and pollution levels may thus be made accessible to the system.

Suitably, the medicament dispenser additionally comprises a data input system for user input of data to the electronic data management system. Preferably, the data input system comprises a man machine interface (MMI) preferably selected from a keypad, voice recognition interface, graphical user interface (GUI) or biometrics interface.

Suitably, the system additionally comprises a visual display unit for display of data from the electronic data management system to the user. The display may for example, comprise a screen such as an LED or LCD screen. More preferably the visual display unit is associable with the housing.

Suitably, the medicament dispenser additionally comprises a datalink for linking to a local data store to enable communication of data between the local data store and the electronic data management system. The datastore may also comprise data management, data analysis and data communication capability.

The datastore may itself form part of a portable device (e.g. a handheld device) or it may be sized and shaped to be accommodated within the patient's home. The datastore may also comprise a physical storage area for storage of replacement medicament containers. The datastore may further comprise a system for refilling medicament from a reservoir of medicament product stored therewithin. The datastore may further provide an electrical recharging system for recharging any electrical energy store on the medicament dispenser, particularly a battery recharging system.

The datalink may for example enable linking with a docking station, a personal computer, a network computer system or a set-top box (e.g. television set-top box) by any suitable method including a hard-wired link, an infra red link or any other suitable wireless communications link.

Suitably, the electronic data management system includes a predictive algorithm or look-up table for calculating the optimum amount of medicament to dispense.

Suitably, the memory on the electronic data management system includes a dose memory for storing dosage data and reference is made to the dose memory in calculating the optimum amount of medicament to dispense.

Suitably, the medicament dispenser additionally comprises a selector for selecting the amount of medicament to dispense from said dispensing mechanism. In one aspect, the selector is manually operable. In another aspect, the selector is operable in response to a signal from the transmitter on the electronic data management system.

Suitably, the medicament dispenser additionally comprises a geographic positioning system such as a global positioning system or a system which relies on the use of multiple communications signals and a triangulation algorithm.

In one aspect, the system is suitable for the delivery of respirable medicament and additionally comprises a sensor which senses the breath of a user, wherein the sensor communicates breath data to the electronic data management system.

In one aspect, the sensor comprises a breath-movable element which is movable in response to the breath of a patient. More preferably, the breath-movable element is selected from the group consisting of a vane, a sail, a piston and an impeller.

In another aspect, the sensor comprises a pressure sensor for sensing the pressure profile associated with the breath of a user.

In a further aspect, the sensor comprises an airflow sensor for sensing the airflow profile associated with the breath of a user.

In a further aspect, the sensor comprises a temperature sensor for sensing the temperature profile associated with the breath of a user. The temperature of the inhaled and exhaled part of the breath cycle varies and may, thus, be used as a measurement tool.

In a further aspect, the sensor comprises a moisture sensor for sensing the moisture profile associated with the breath of a user. The moisture content of the inhaled and exhaled part of the breath cycle varies and this also may be used as a measurement tool.

In a further aspect, the sensor comprises a gas sensor for sensing the oxygen or carbon dioxide profile associated with the breath of a user. The chemical profile of the inhaled and exhaled part of the breath cycle varies and this further may be used as a measurement tool.

Suitably, the breath data includes breath cycle data, $FEV_1$ and/or peak flow data.

Suitably, the medicament dispenser additionally comprises release means for releasing medicament from said medicament container; a breath trigger for triggering the release means, said breath trigger being actuable in response to a trigger signal from the electronic data management system. Preferably, the electronic data management system includes a predictive algorithm or look-up table for deriving from the breath data when to transmit the trigger signal. For example, a real-time analysis of the patient breath waveform may be made and the trigger point derived by reference to that analysed waveform.

Suitably, the medicament container is an aerosol container. Suitably, the aerosol container comprises a suspension of a medicament in a propellant. Suitably, the propellant comprises liquefied HFA134a, HFA-227 or carbon dioxide. In one aspect, the aerosol container comprises a solution of a medicament in a solvent.

Suitably, the medicament container is for the containment of medicament in tablet or nebule form.

Suitably, the medicament container is a dry-powder container. In one aspect, the container comprises a reservoir for dry powder medicament which is accessible by a metering means for metering (e.g. a dose of) medicament therefrom. In another aspect, the medicament container comprises one or individual capsules or blisters for containing defined amounts of powdered medicament. Multi-unit dose blisters in elongate strip form are particularly envisaged.

Suitably, the dry-powder container comprises medicament and optionally excipient in dry-powder form.

Where the medicament container is an aerosol container the release means typically comprises a valve mechanism. Where the medicament container comprises a dry powder reservoir the release means typically co-operates with the aforementioned metering means for metering (e.g. a dose of) medicament therefrom. Where the medicament container comprises one or more individual capsules or blisters the release means typically comprises means for rupturing, peeling apart or otherwise accessing the contents thereof.

Suitably, the medicament is selected from the group consisting of albuterol, salmeterol, fluticasone propionate, ipratropium bromide beclomethasone dipropionate, salts or solvates thereof and any mixtures thereof. Suitable combination products comprise salmeterol xinafoate and fluticasone propionate; or salmeterol and ipratropium bromide.

The medicament dispenser herein may also be in the form of a syringe. Traditional syringes rely on puncturing of the patient's skin by a hollow needle through which the injectable medicament (in solution or suspension form) is delivered to the muscle or tissue of the patient from a medicament container (e.g. in the form of a syringe barrel). Recently developed needleless systems for the delivery of injectables employ high velocity injection of particle formulated drugs or vaccine through the skin and into any physically accessible tissue. Other needleless systems employ similar high velocity injection of drug or vaccine coated on to a suitable carrier particle. Such needleless systems may be configured to include a source of compressed air or gas, which on release provides energy to propel the medicament particles for injection into the skin.

According to another aspect of the present invention there is provided a kit of parts comprising a medicament dispenser comprising a body, said body shaped for receipt of a medicament container; in association with the body, a first transceiver for transmitting and receiving data; and a medicament container receivable by the body of the medicament dispenser; and in association with the medicament container, a second transceiver for transmitting and receiving data, wherein data is transferable in two-way fashion from the first transceiver to the second transceiver.

In one aspect, the data is transferable in two-way fashion from the first transceiver to the second transceiver only when the medicament container is received within the body of the medicament dispenser.

In one aspect, the kit of parts is arranged such that the medicament dispenser comprises parts which are reusable (i.e. typically expensive) and the medicament container comprises parts which are disposable (i.e. typically cheap) or recyclable.

In aspects, the medicament dispenser may therefore be arranged to comprise reusable elements selected from the group consisting of an outer casing; a first transceiver; an electronic data management system; an electronic display; a rechargeable battery; and optionally various sensors. The medicament container on the other hand is arranged to comprise disposable/recyclable elements selected from the group consisting of a disposable medicament pack; a disposable battery; a disposable second transceiver; and optionally a disposable mouthpiece/release means.

According to another aspect of the present invention there is provided a system comprising a medicament dispenser as described herein before including an electronic data management system; and a remote data management system, wherein data is transferable between the electronic data management system of the medicament dispenser and the remote data management system. The term remote is used to mean that the remote data management system forms part of a system or device which is separate from the medicament dispenser.

In one aspect, the remote data management system comprises a local data store e.g. as described hereinbefore.

In another aspect, the remote data management system comprises a network computer system e.g. as described hereinbefore.

BRIEF DESCRIPTION OF THE FIGURES

Embodiments according to the invention will now be described with reference to the accompanying drawings in which.

DETAILED DESCRIPTION

Figure 1A:
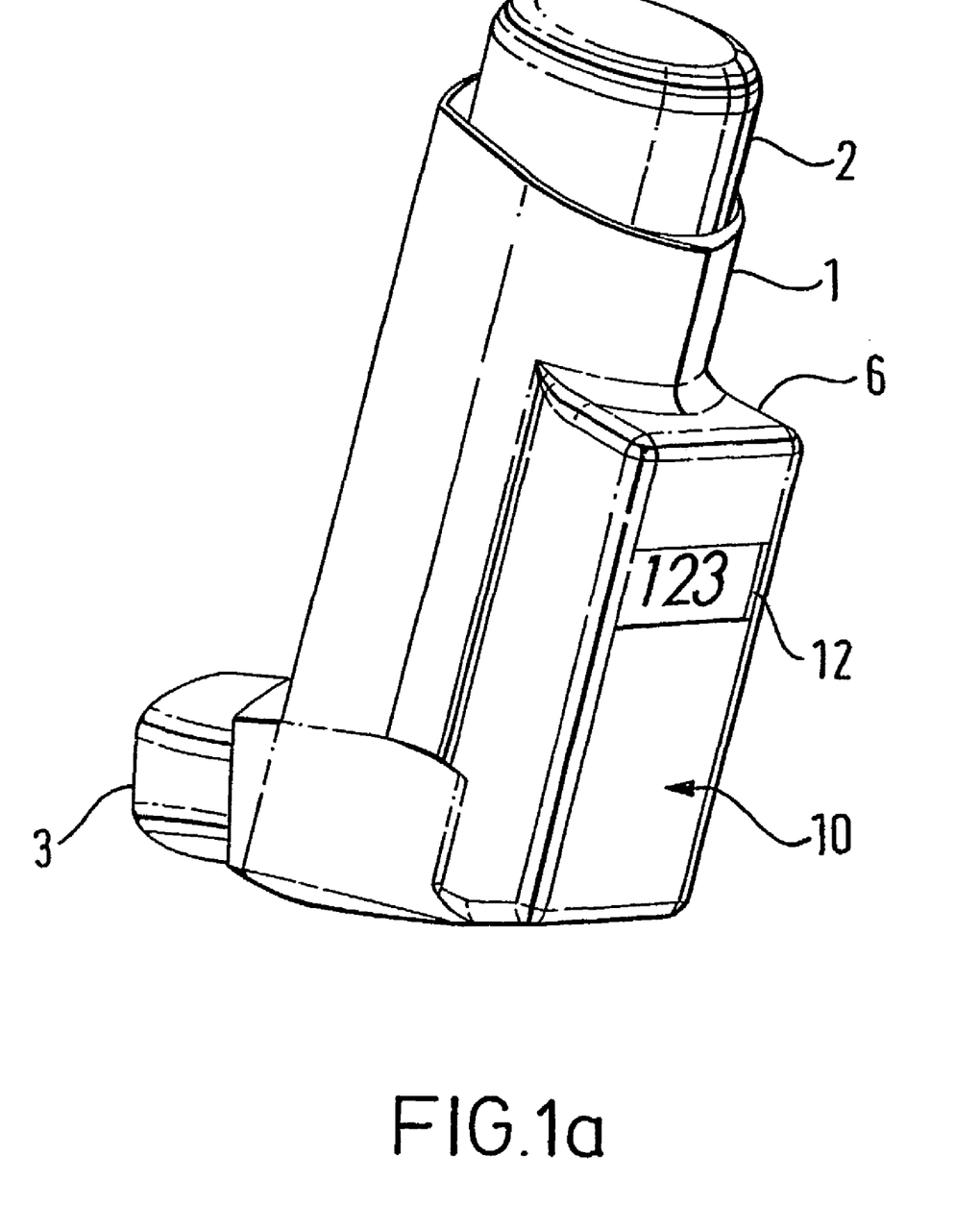
FIGS. 1a and 1b show representations of a metered dose inhaler herein in assembled form and separated into its component parts of housing and aerosol container.
Figure 1B:
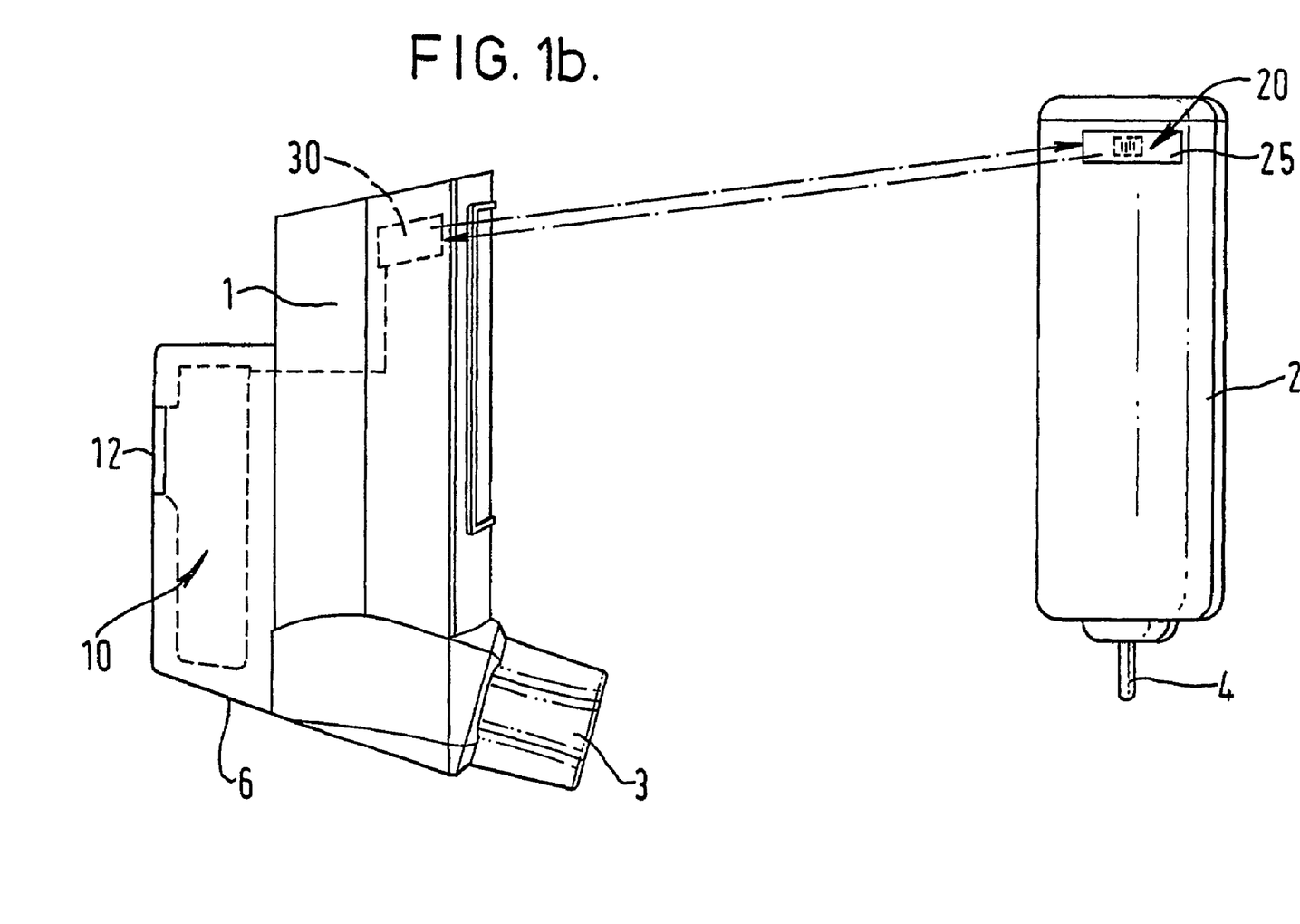

FIGS. 1a and 1b show a metered dose inhaler comprising a tubular actuator housing 1 shaped for receipt of an aerosol container 2. The actuator housing is open at one end and is closed at the other. An outlet 3 leads laterally from the closed end of the housing 1. In the embodiment illustrated, the outlet 3 is in the form of a mouthpiece intended for insertion into the mouth of the patient but it may, if desired, be designed as a nozzle for insertion into the patient's nostril. The aerosol container 2 has an outlet valve 4 at one end. This valve acts as a release means for release of a measured dose from the aerosol container. The release means is actuable by inward movement of the valve 4 relative to the aerosol container 2.

The metered dose inhaler of FIGS. 1a and 1b includes an electronic data management system 10 comprised within an extended part of the housing 6. Visual display monitor 12 allows for display of information from the electronic data management system 10 to the patient. The electronic data management system 10 connects to a sensor (not visible) for sensing the breathing pattern of the patient and an actuator (not visible) for actuating the release of aerosol from the container 2.

A passive transceiver in the form of a tag 20 on an inert carrier 25 is mounted on the side of the aerosol container 2. An active transceiver in the form of a reader 30 for the tag 20 is moulded into the internal surface of the housing 1. The reader 30 is capable of data communication with the electronic data management system 10. The reader 30 is also capable of reading and writing information to the tag 20 mounted on the aerosol container 2 by transmission and receipt of energy to/from the tag 20 (shown as broken arrows).

In one embodiment the tag 20 comprises a radiofrequency identification tag and the active transceiver 30 is capable of reading data therefrom and writing data thereto by the use of interrogating radiofrequency energy. In another embodiment the tag 20 comprises a magnetic label and the active transceiver 30 is capable of reading data therefrom and writing data thereto by the use of interrogating magnetic field energy.

Figure 2:
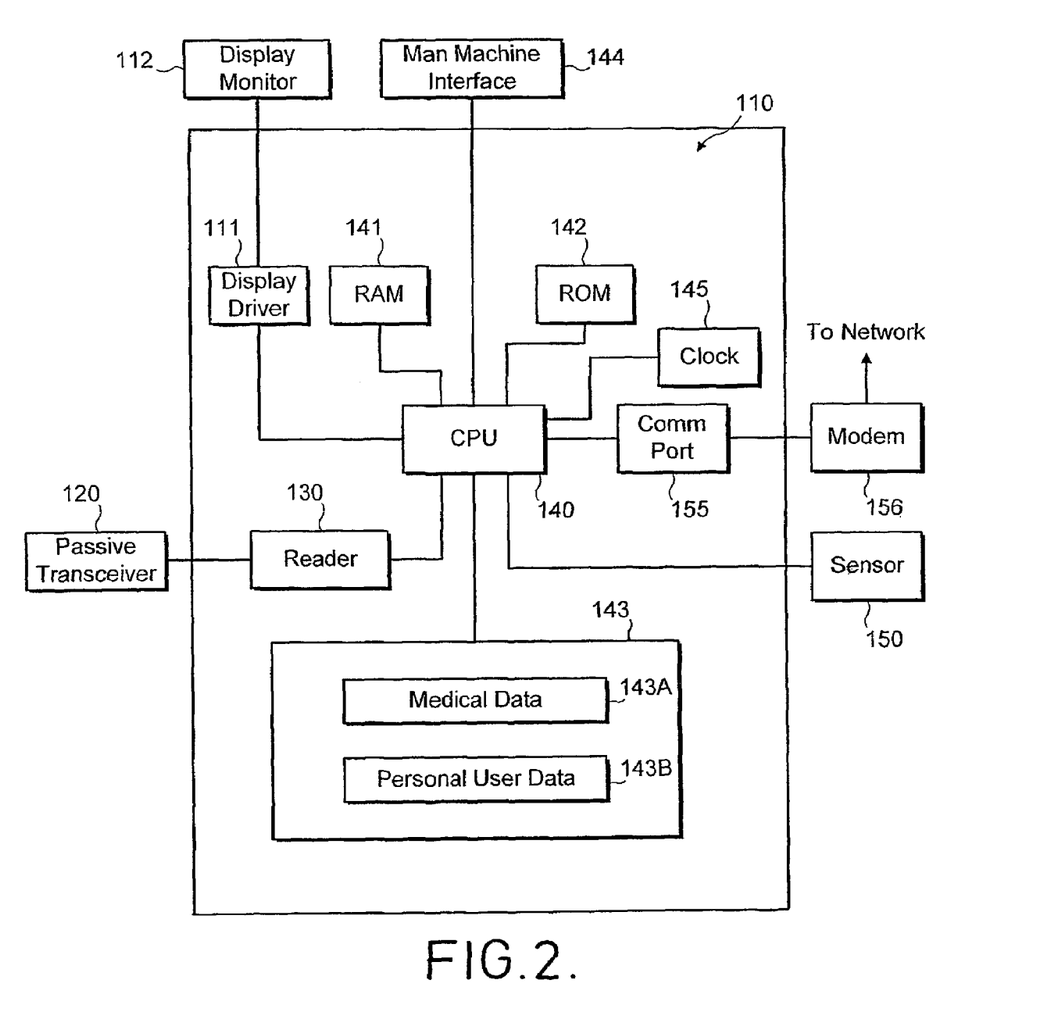
FIG. 2. shows a schematic representation of an electronic data management system for use herein.

FIG. 2 shows the structure of an electronic data management 110 comprised within the housing of a respiratory drug delivery system (not shown). The electronic data management system 110 could for example be employed in the metered dose inhaler shown in FIGS. 1a and 1b. The data management system 110 comprises a central processor unit (CPU) 140, RAM 141 and ROM 142. The CPU 140 is capable of two-way data transfer with reader 130. The reader is capable of reading and writing information to a passive transceiver in the form of a tag 120 (e.g. on a medicament container). The tag 120 may comprise an RFID tag or a magnetic tag. As in FIGS. 1a and 1b, the reader 130 will form part of the housing of the drug delivery system and the tag 120 will be mounted on a reloadable medicament container receivable thereby. The CPU 140 also receives patient data from sensor 150 which may for example be a breath sensor or a sensor detecting actuation of the drug delivery system. The received data is storable in data storage device 143 which includes two databases, one for storage of medical data 143a and one for storage of personal patient data 143b. The CPU 140 is also associated with man machine interface 144 for receipt of patient input commands; clock 145; and display driver 111 and display 112 for display of information to the patient. The CPU 140 is further associated with communications port 155 which links via modem 156 to a network computer system (not shown) to enable communication therewith.

Figure 3A:
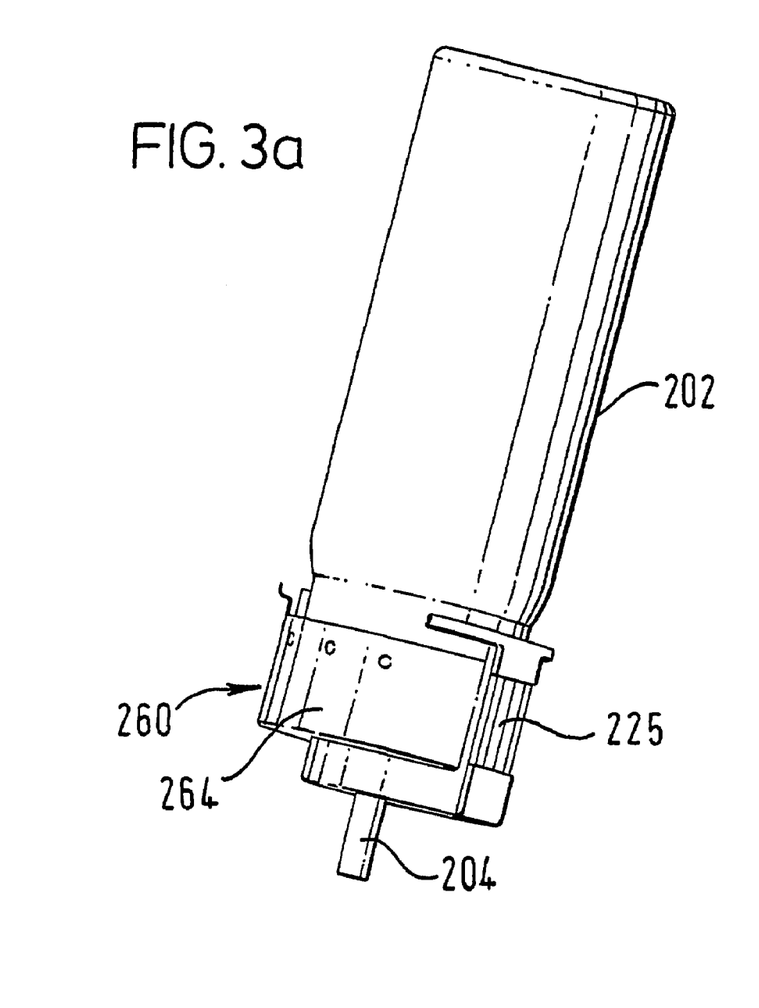
FIGS. 3a and 3b show a ring collar attachment for an aerosol container for use in a metered dose inhaler.
Figure 3B:
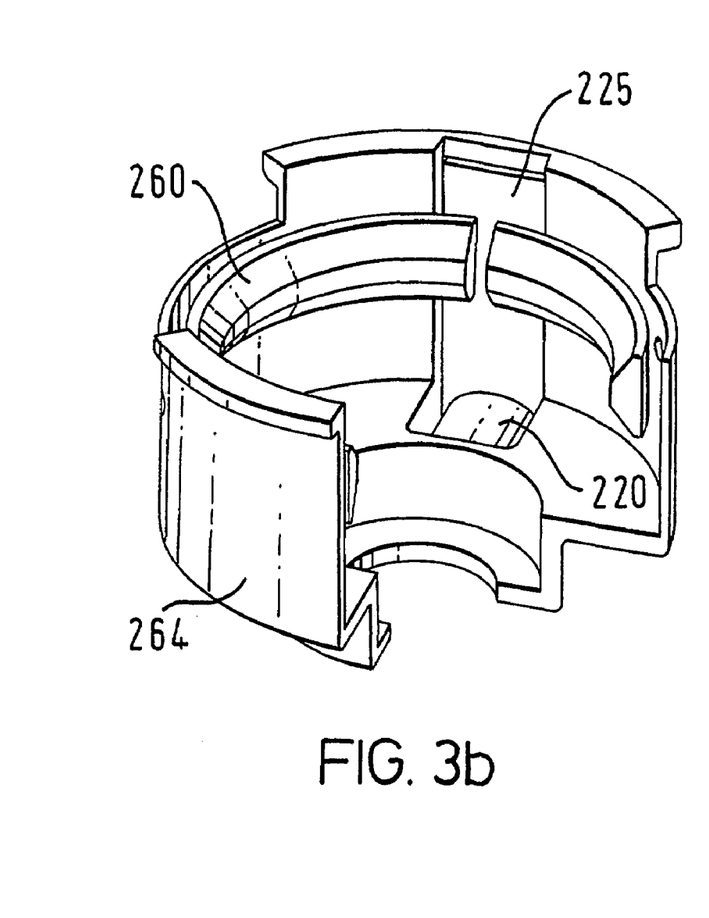

FIGS. 3a and 3b show a collar ring 260 which is shaped for attachment to the neck of an aerosol container 202 (shown in FIG. 3a only) having a dispensing stem 204 for use in a metered dose inhaler. The collar ring includes weld ring 264 for welding the collar 260 to the aerosol container 202. The collar ring also includes passive transceiver in the form of an electrically erasable programmable read only memory (EEPROM) chip 220. The chip 220 communicates with electrical contact pad 225.

Figure 4:
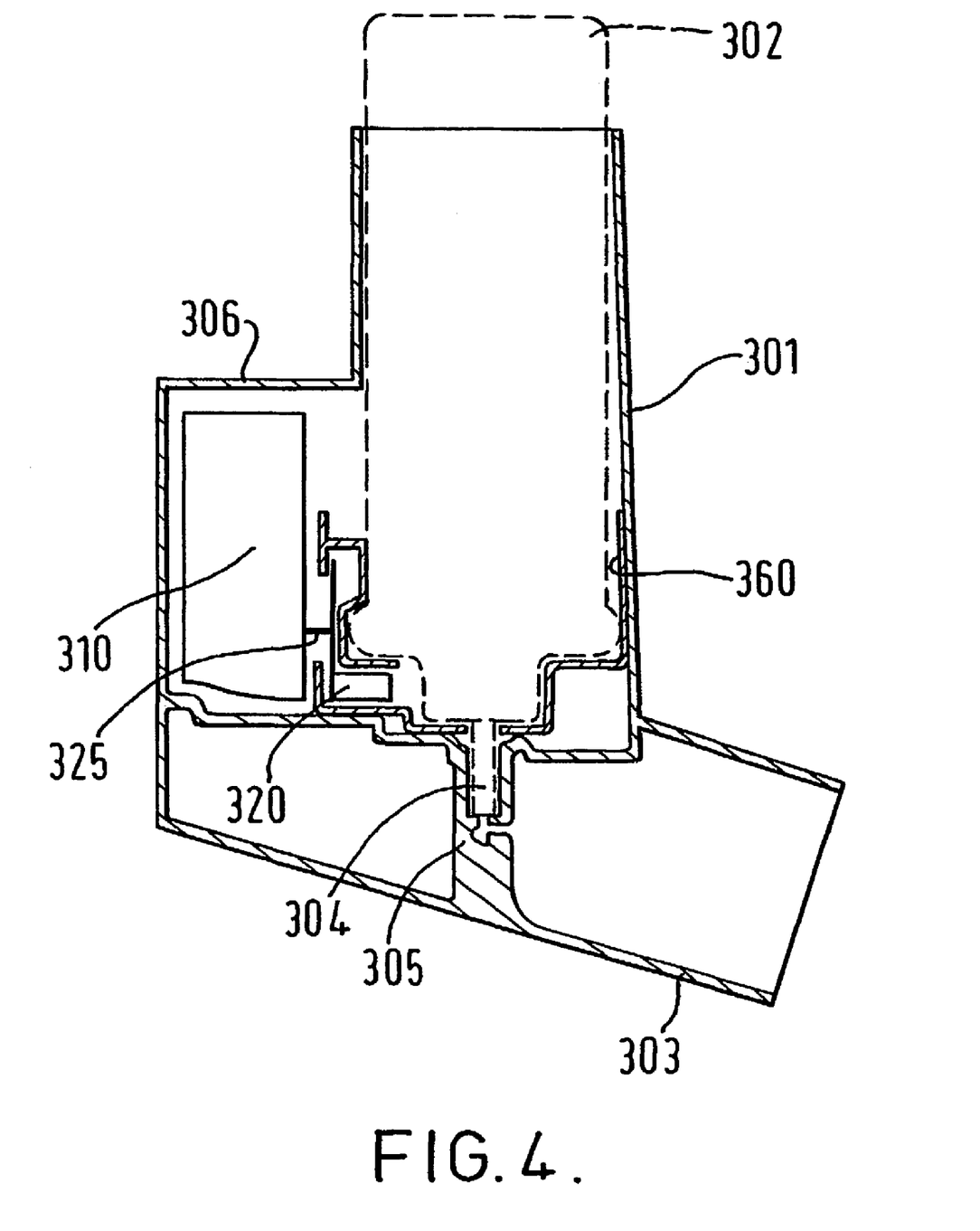
FIG. 4 shows a sectional view of an actuator housing suitable for receiving an aerosol container with ring attachment as shown in FIGS. 3a and 3b.

FIG. 4 shows an actuator housing 301 in the form of a metered dose inhaler shaped for receipt of aerosol container 302 having a collar ring 360 (as shown in FIGS. 3a and 3b). The housing has an outlet in the form of a mouthpiece 303 and an actuator block with dispensing nozzle 305 shaped for receipt of the valve stem 304 of the aerosol container. The rear part of the housing 301 is extended 306 to accommodate an electronic data management system 310 (not shown in detail). Passive transceiver 320 in the form of EEPROM on the collar ring 360 communicates with the data management system 310 via electrical contact 325. The data management system 310 includes a reader for the passive transceiver 320. Data may therefore be transferred in read/write fashion between the electronic data management system 310 and the passive transceiver 320.

Figures 5A, 5B:
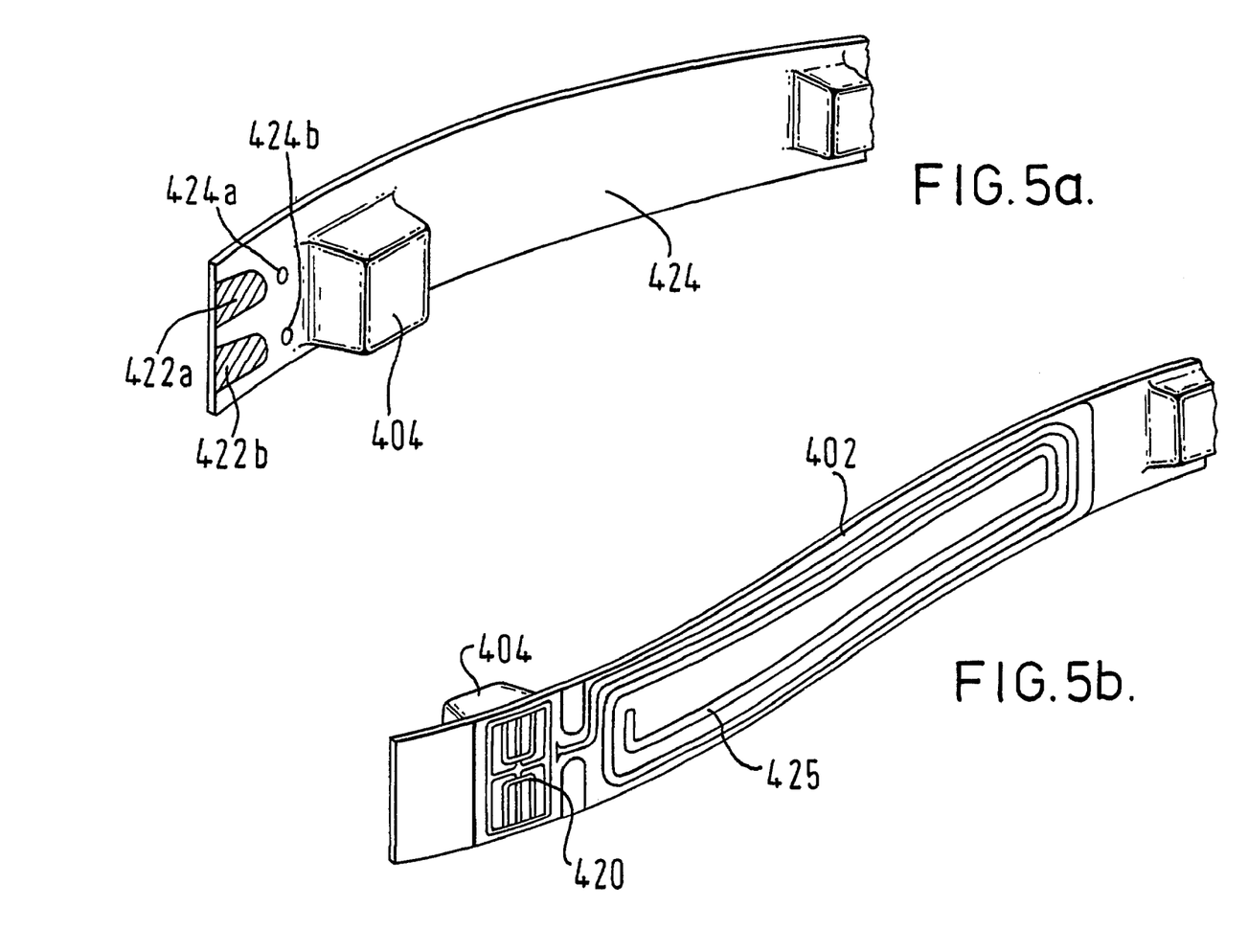
FIGS. 5a and 5b show a medicament container herein in the form of an elongate blister strip.

FIGS. 5a and 5b show a medicament container 402 in the form of an elongate strip comprising a blister 404 for containment of powdered medicament. Whilst for simplicity only one blister 404 is shown it will be appreciated that variations could comprise multiple blisters (e.g. arranged in axial fashion). As visible in FIG. 5b, the reverse of the blister 404 is provided with a tag 420 in the form of an electronic memory chip. In one aspect, power is supplied to the chip 420 by means of electrical contacts 422b, 422a in communication with electrical inputs 424a, 424b. The chip 420 connects with antenna 425 which enables transfer of energy/data to the chip 420.

The blister strip 402 of FIGS. 5a and 5b is designed for receipt by a medicament dispenser (not shown) for which it would comprise a medicament refill pack. Multi-unit dose blister type dispensers for dry powder medicament are known in the art, including the device sold by GlaxoSmithKline under the trade mark Diskus as for example described in U.S. Pat. No. 6,032,666.

The medicament dispenser of the present invention is in one aspect suitable for dispensing medicament for the treatment of respiratory disorders such as disorders of the lungs and bronchial tracts including asthma and chronic obstructive pulmonary disorder (COPD).

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. s the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (eg as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (eg as free base or sulphate), salmeterol (eg as xinafoate), ephedrine, adrenaline, fenoterol (eg as hydrobromide), formoterol (eg as fumarate), isoprenaline, metaproterenol, phenylephrine, phenylpropanolamine, pirbuterol (eg as acetate), reproterol (eg as hydrochloride), rimiterol, terbutaline (eg as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, eg 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); α4 integrin inhibitors eg (2S)-3-[4-({[4-(aminocarbonyl)-1-piperidinyl]carbonyl}oxy)phenyl]-2-[((2S)-4-methyl-2-{[2-(2-methylphenoxy) acetyl]amino}pentanoyl) amino] propanoic acid (e.g as free acid or potassium salt), diuretics, e.g., amiloride; anticholinergics, e.g., ipratropium (eg as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (eg as the fumarate salt) in combination with an anti-inflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt). A further combination of particular interest is salmeterol, or a salt thereof (particularly the xinafoate salt) and ipratropium bromide.

The medicament dispenser of the present invention is in another aspect a syringe for the delivery of injectable medicament to a patient. Traditional syringes rely on puncturing of the patient's skin by a hollow needle through which the injectable medicament (in solution or suspension form) is delivered to the muscle or tissue of the patient. Recently developed needleless systems for the delivery of injectables employ high velocity injection of particle formulated drugs or vaccine through the skin and into any physically accessible tissue. Other needleless systems employ similar high velocity injection of drug or vaccine coated on to a suitable carrier particle.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. A metered dose inhaler comprising
   an actuator housing shaped for receipt of an aerosol container;
   in association with the actuator housing, a first transceiver for transmitting and receiving data;
   an aerosol container receivable by the actuator housing; and in association with the aerosol container, a second transceiver for transmitting and receiving data,
wherein data is transferable in two-way fashion from the first transceiver to the second transceiver in the absence of direct physical contact between the first and second transceiver, and
wherein the second transceiver comprises a tag comprising
an antenna for transmitting or receiving energy; and
an integrated circuit chip connecting with said antenna,
and the first transceiver comprises a reader for said tag,
wherein the integrated circuit chip has a memory area with restricted read access.

2. A metered dose inhaler comprising
an actuator housing shaped for receipt of an aerosol container;
in association with the actuator housing, a first transceiver for transmitting and receiving data;
an aerosol container receivable by the actuator housing; and
in association with the metered dose inhaler, a second transceiver for transmitting and receiving data,
wherein data is transferable in two-way fashion from the first transceiver to the second transceiver in the absence of direct physical contact between the first and second transceiver, and
wherein the second transceiver comprises a tag comprising
an antenna for transmitting or receiving energy; and
an integrated circuit chip connecting with said antenna,
wherein the integrated circuit chip has a read/write memory area.

3. A metered dose inhaler comprising
an actuator housing shaped for receipt of an aerosol container;
in association with the actuator housing, a first transceiver for transmitting and receiving data;
an aerosol container receivable by the actuator housing; and
in association with the aerosol container, a second transceiver for transmitting and receiving data,
wherein data is transferable in two-way fashion from the first transceiver to the second transceiver in the absence of direct physical contact between the first and second transceiver, and
wherein the second transceiver comprises a tag comprising
an antenna for transmitting or receiving energy; and
an integrated circuit chip connecting with said antenna,
wherein the integrated circuit chip has a one-time programmable memory area.

4. A metered dose inhaler according to claim 3, wherein the one time programmable memory area contains a unique serial number.

5. A metered dose inhaler comprising
an actuator housing shaped for receipt of an aerosol container;
in association with the actuator housing, a first transceiver for transmitting and receiving data;
an aerosol container receivable by the actuator housing; and
in association with the aerosol container, a second transceiver for transmitting and receiving data,
wherein data is transferable in two-way fashion from the first transceiver to the second transceiver in the absence of direct physical contact between the first and second transceiver, and
wherein the second transceiver comprises a tag comprising
an antenna for transmitting or receiving enemy; and
an integrated circuit chip connecting with said antenna,
wherein the integrated circuit chip has a preset memory area containing a non-changeable data item.

6. A metered dose inhaler comprising
an actuator housing shaped for receipt of an aerosol container;
in association with the actuator housing, a first transceiver for transmitting and receiving data;
an aerosol container receivable by the actuator housing; and
in association with the aerosol container, a second transceiver for transmitting and receiving data,
wherein data is transferable in two-way fashion from the first transceiver to the second transceiver in the absence of direct physical contact between the first and second transceiver, and
wherein the second transceiver comprises a tag comprising
an antenna for transmitting or receiving energy; and
an integrated circuit chip connecting with said antenna,
wherein the integrated circuit chip has plural memory areas thereon.

7. A metered dose inhaler comprising
an actuator housing shaped for receipt of an aerosol container;
in association with the actuator housing, a first transceiver for transmitting and receiving data;
an aerosol container receivable by the body; and
in association with the aerosol container, a second transceiver for transmitting and receiving data,
wherein data is transferable in two-way fashion from the first transceiver to the second transceiver in the absence of direct physical contact between the first and second transceiver, and
wherein the second transceiver comprises a tag comprising
an antenna for transmitting or receiving energy; and
an integrated circuit chip connecting with said antenna,
wherein any memory area on the integrated circuit chip contains data in encrypted form.

8. A metered dose inhaler comprising
An actuator housing shaped for receipt of an aerosol container;
in association with the actuator housing, a first transceiver for transmitting and receiving data;
an aerosol container receivable by the actuator housing; and
in association with the aerosol container, a second transceiver for transmitting and receiving data,
wherein data is transferable in two-way fashion from the first transceiver to the second transceiver in the absence of direct physical contact between the first and second transceiver, and
wherein the second transceiver comprises a tag comprising
an antenna for transmitting or receiving energy; and
an integrated circuit chip connecting with said antenna,
wherein any memory area on the integrated circuit chip is password protected.

9. A metered dose inhaler comprising
an actuator housing shaped for receipt of an aerosol container;
in association with the actuator housing, a first transceiver for transmitting and receiving data;
an aerosol container receivable by the actuator housing; and
in association with the aerosol container, a second transceiver for transmitting and receiving data, wherein data is transferable in two-way fashion from the first transceiver to the second transceiver in the absence of direct physical contact between the first and second transceiver, and wherein the second transceiver comprises a tag comprising
an antenna for transmitting or receiving energy; and
an integrated circuit chip connecting with said antenna,
wherein the integrated circuit has plural memory areas thereon including
(a) a read only memory area containing a unique serial number;
(b) a read/write memory area which can be made read only; and
(c) a password protected memory area containing data in encrypted form.

10. A metered dose inhaler comprising
an actuator housing shaped for receipt of an aerosol container;
in association with the actuator housing, a first transceiver for transmitting and receiving data;
an aerosol container receivable by the actuator housing; and
in association with the aerosol container, a second transceiver for transmitting and receiving data,
wherein data is transferable in two-way fashion from the first transceiver to the second transceiver in the absence of direct physical contact between the first and second transceiver, and
wherein the second transceiver comprises a tag comprising
an antenna for transmitting or receiving energy; and
an integrated circuit chip connecting with said antenna,
wherein the second transceiver comprises a passive microelectronic memory chip and the first transceiver comprises an active reader for said microelectronic memory chip.

* * * * *